United States Patent [19]

Unger

[11] Patent Number: 5,458,123
[45] Date of Patent: Oct. 17, 1995

[54] SYSTEM FOR MONITORING PATIENT LOCATION AND DATA

[75] Inventor: John D. Unger, Windham, N.H.

[73] Assignee: Siemens Medical Systems, Inc., Iselin, N.J.

[21] Appl. No.: 235,208

[22] Filed: Apr. 29, 1994

Related U.S. Application Data

[63] Continuation of Ser. No. 991,636, Dec. 16, 1992, abandoned.

[51] Int. Cl.⁶ .............................. H04B 1/00; G08C 17/00
[52] U.S. Cl. .................... 128/696; 128/903; 340/870.41; 181/115
[58] Field of Search .............................. 340/573, 870.41, 340/825.36, 825.54; 128/630, 637, 671, 680, 687, 696, 776, 903; 181/125; 329/370; 367/117

[56] References Cited

U.S. PATENT DOCUMENTS

| | | | |
|---|---|---|---|
| 3,478,344 | 6/1965 | Schwitzgebel et al. | 128/903 |
| 3,986,498 | 10/1976 | Lewis | 128/2.06 R |
| 4,916,444 | 4/1990 | King | 340/825.36 |
| 4,952,928 | 8/1990 | Carroll et al. | 128/903 |
| 4,955,000 | 9/1990 | Nastrom | 367/117 |
| 4,958,645 | 9/1990 | Cadell et al. | 128/903 |
| 4,981,141 | 1/1991 | Segalowitz | 128/696 |
| 5,153,584 | 10/1992 | Engira | 128/903 |

Primary Examiner—William E. Kamm
Assistant Examiner—Marianne Parker
Attorney, Agent, or Firm—Lawrence C. Edelman

[57] ABSTRACT

A patient monitoring system utilizes a transmitter associated with each patient. The transmitter is worn by a patient and includes sensors operative to monitor vital signs of the patient. The transmitter transmits an allocated RF frequency which is particularly associated with that patient. A series of antennas are incorporated in a building, each antenna having its own signature signal. As the patient moves throughout the building, the antennas pick up the signals from the patient's transmitter and combines the antenna signature signal with the transmitted patient signal. This combined signal is then analyzed at a central location to determine the exact location of the patient due to the antenna signature signal which is modulated on the transmitted patient signal. Transmitted patient data is also decoded at the central station to provide a signal indicative of the vital signs of the patient.

17 Claims, 2 Drawing Sheets

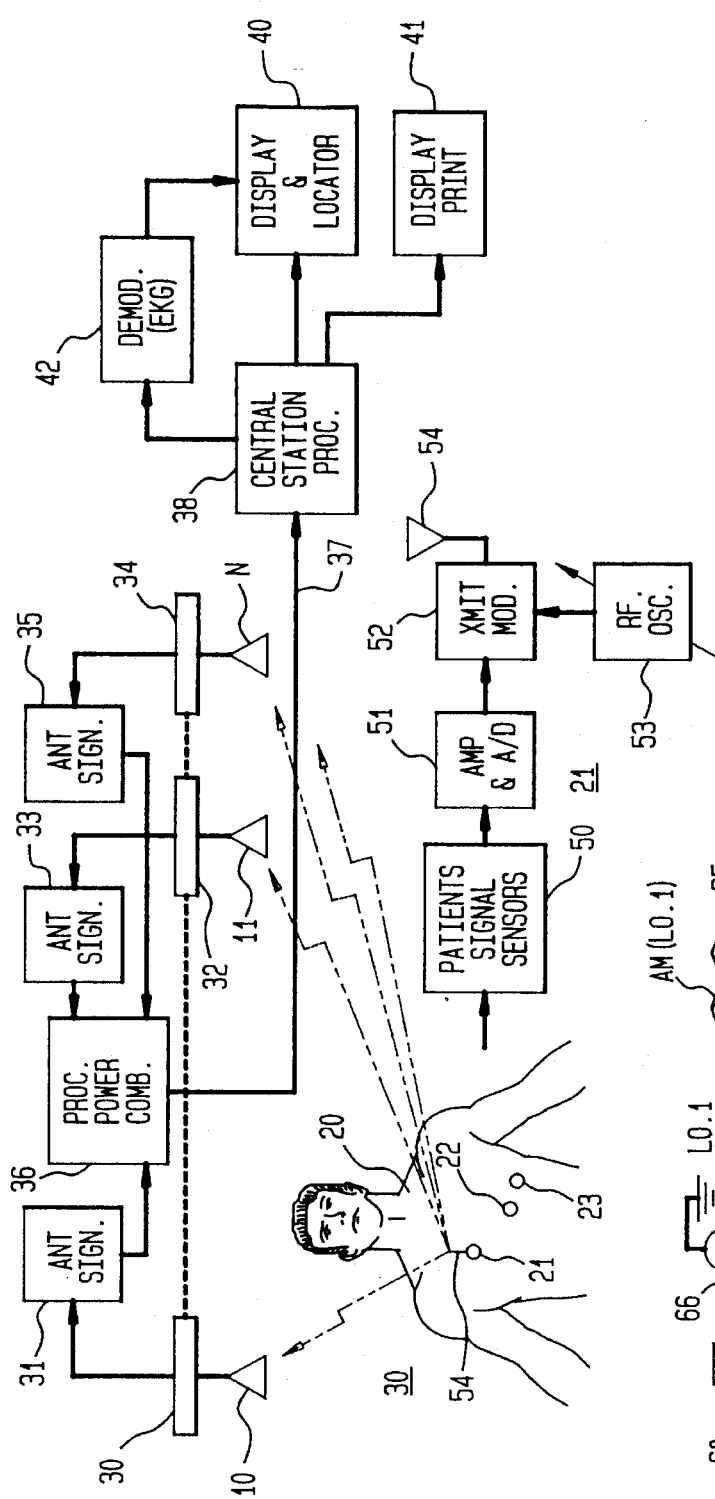
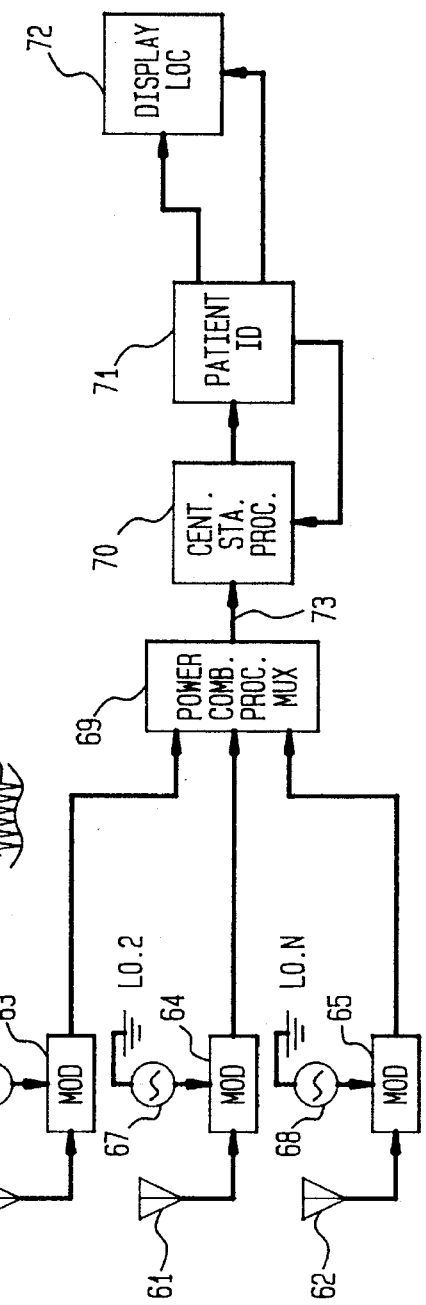
FIG. 1
FIG. 2

5,458,123

SYSTEM FOR MONITORING PATIENT LOCATION AND DATA

CROSS-REFERENCE TO RELATED APPLICATION

This is a continuation of Ser. No. 07/991,636 filed Dec. 16, 1992, now abandoned.

FIELD OF THE INVENTION

This invention relates to a medical instrumentation system and more particularly to a system for monitoring the location of a patient within a hospital or other area and for receiving data from that patient.

BACKGROUND OF INVENTION

The prior art is replete with various systems which operate to monitor patients for providing patient data to a central location. Such systems can be bedside systems whereby the patient is confined to a bed and is suitably connected to sensors so that physiological medical information is transmitted to a central location by means of cables or other means. Such systems are employed in the intensive care units (ICU) of hospitals where vital signs such as temperature, respiration, heart rate and so on of a patient are monitored.

Some modern techniques utilize wireless transmission, such as telemetry systems, whereby a patient is furnished with a transmitter and receiver. Sensors placed on the patient monitor electrical signals produced by the patient to provide e.g., EKG signals. These signals are then converted to other signals which can be transmitted by antennas, conventional radio links or by other radio frequency (RF) techniques. Existing ambulatory systems can provide various signals relating to the monitoring of e.g., the patient's temperature, heart rate and so on. Essentially, the type of medical data which can be transmitted by such systems includes any type of data which can be measured by conventional sensors which are applied to the skin or otherwise implanted in the patient. There are systems which also will give an indication of the location of the patient.

A typical prior art system is described in U.S. Pat. No. 4,958,645 entitled MULTI-CHANNEL DIGITAL MEDICAL TELEMETRY SYSTEM, which issued on Sep. 25, 1990 to Theodore E. Cadell et al. and is assigned to CME Telemetrix, Inc. of Canada. The medical radio telemetry system described therein utilizes a plurality of antennas which are distributed throughout a hospital or other premises. The patient is outfitted with a radio receiver and transmitter which unit is operative to collect data such as temperature, heart rate, pacer rate, respiration rate, brain activity level and blood pressure level. The transmitter and receiver associated with the patient operates in conjunction with one or more room locator transmitters. The room locator transmitters are spaced in rooms or about the area where the patient is being monitored. The signal from the patient's transmitter is passed to the room transmitters. All signals received by the patient are transmitted to an antenna system that is connected to a receiver. As indicated there is one or more antenna systems with means for switching between the systems to obtain the best signal. In the system, the patient also receives a signal from any one of the room locator transmitters and the patients unit transmits the received signal together with his EKG signal.

The transmitting antenna system transmits the signals to the receiving antenna which is connected to a receiver whereby the patient can be monitored at a remote location such as a central nursing location in a hospital. In this manner, all data which is being provided by the patient is transmitted to the central location and the data is transmitted together with a location signal received by the patient's receiver module. Thus, the location of the patient is known because the patient receives a location signal which is transmitted by the patient. Thus, the system enables the hospital staff to monitor patients and in the event of a particular medical problem the patient's position is immediately ascertained as well. There are other systems which monitor the status of the patient utilizing networking techniques.

U.S. Pat. No. 4,981,141 entitled WIRELESS ELECTROCARDIOGRAPHIC MONITORING SYSTEM issued on Jan. 1, 1991 to J. Segalowitz. This patent describes a stationary electrocardiographic monitoring system where the patient's heart-signaling sensing electrodes are each coupled to the heart-signal monitor/recorder by respective ones of wireless transmitters and corresponding respective wireless receivers in a base unit. Each transmitter/receiver combination operates at a separate radio frequency to provide a zero or reference signal at a base unit and which is used to modulate a signal transmitter at the base unit. Each modulated signal, when received and demodulated provides information concerning signal sensed by a respective electrode carried by the patient, as for example, the right-leg electrode, etc.

It should be obvious from the above that it is extremely desirable to monitor a patient who is ambulatory in regard to various vital signs, such as heart rate and so on. This is even more important due to the recent trend to get patients ambulating as soon as possible. Thus, it is also important to determine the location of this patient within, for example, the confines of a hospital or other area. As one can ascertain, many modern hospitals have a great number of floors and are spread over wide areas. Since an ambulatory patient may experience a medical problem as a heart attack, the monitoring system should detect this at a central location and furthermore, receive information regarding the location of the patient within the hospital.

Thus, patients who are post-coronary or other at-risk patients should be monitored in regard to their vital signs and a position signal provided to determine the precise location of the patient within a large medical facility or some other area.

While the invention has particular applicability in determining the location of a monitored patient it is understood that the techniques described herein can be utilized for other purposes, such as for locating children in large shopping centers and so on.

It is an object of the present invention to provide both a vital sign monitoring and patient locating system which is efficient and economical. The described system enables one to monitor the vital signs and the location of the patient without requiring the patient to be provided with a separate receiving apparatus as implemented in the prior art.

SUMMARY OF INVENTION

In a patient monitoring telemetry system employing a plurality of antennas located throughout an operating area and where a patient wears a transmitter capable of transmitting a patient signal containing data indicative of at least one monitored vital sign of the patient, the antennas adapted to receive the transmitted patient signal for directing the same to a central location for demodulating the signal so as to provide data indicative of the monitored vital signs of the patient, the improvement in combination therewith of apparatus for providing the central location with information indicative of the location of the patient within the operating area as determined by the patient being located near a given one antenna of the plurality, the apparatus comprising antenna signature means coupled to each antenna and operative to provide a unique signal for each associated antenna, which signal is combined with a received patient signal by the antenna, whereby each antenna of the plurality has a unique signal which is impressed upon any received patient signal to enable the central location to determine which antenna transmitted the signal and therefore indicative of the patient's location within the operating area.

BRIEF DESCRIPTION OF THE FIGURES

FIG. 1 is a block diagram of a system for monitoring patient location and for transmitting patient data according to this invention.

FIG. 2 is a block diagram of an alternate form of the monitoring system according to this invention.

DETAILED DESCRIPTION OF THE FIGURES

Figure 3:
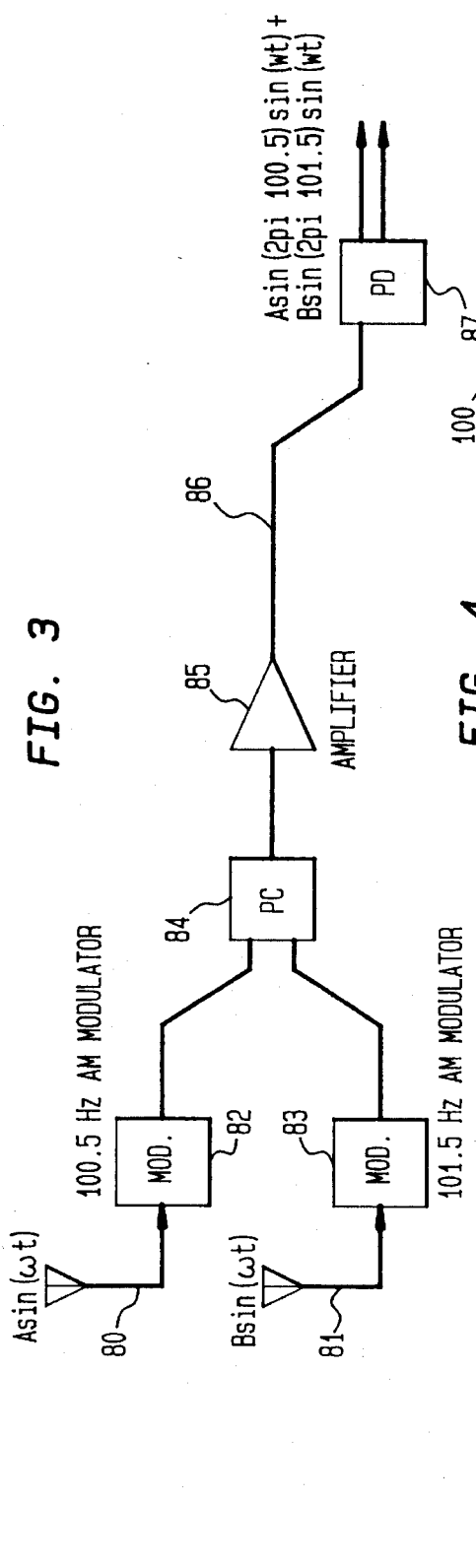
FIG. 3 is a circuit diagram showing a alternate embodiment of this invention.

Referring to FIG. 1 there is shown a system block diagram of a patient monitoring and location system according to this invention. Reference numeral 30 depicts a patient who has included on his person a personal transmitter 21. The transmitter 21 may be coupled to signal sensors or transducers which are connected to the patient either via the patient's skin or other wise. The signals produced are well known. These signals emanate from transducers and are analog signals and can include one or more of characteristics indicative of the patient's health as monitoring vital signs. As such, sensors mounted on the patient 30 as for example sensors 22 and 23 can include temperature sensors, heart rate sensors, pacer rate, respiration rate and various other devices. In particular, the EKG is a very common signal which is to be monitored. The EKG activity information transmitted conforms to normal professional standards and levels of accuracy and many conventional devices are fully capable of measuring the important functions of the heart such as rhythm, rate, p-wave and so on. The techniques for producing EKGs and for transmitting such signals are well know in the art.

As seen in FIG. 1, the patient's transmitter 21 is associated with an antenna which may include the wires which are connected directly to the patient's sensors. As will be explained, each patient is assigned a transmitter 21 which is associated with a unique RF signal. This RF signal is the transmitted carrier signal and serves to differentiate one patient from another. The transmitter basically consists of the patient's signal sensors as indicated by module 50. The signal sensors are typically coupled to module 51 which is designated as amplifier and analog to digital (A/D) converter. In this manner, the patient's signal sensors 50 are amplified and the analog signal is converted to a digital signal. A modulator module 52 is coupled to a RF oscillator 53. The RF oscillator 53 is the carrier frequency for that particular patient and serves to modulate the digital output from the analog to the digital module 51. The transmitter modulator 52 produces an output signal which is coupled to antenna 54 and is transmitted by the patient. In this manner, the transmitter carried by the patient basically operates to transmit the monitored vital sign information, such as the EKG. This information as indicated is converted to digital information and is modulated on the RF carrier and transmitted via the antenna 54. It is understood that the antenna 54 may include the wires associated with the patient's sensors.

As previously explained, some prior art systems employ radio transmitter beacons which are distributed throughout the hospital each of which transmits a unique location code continuously. These transmitter beacons may be located at various floors and various rooms about the hospital. The patient using such prior art systems has a receiver which is associated with his telemetry transmitter and which receiver picks up the transmitted beacon signals, combines the transmitted beacon signal with the EKG data and then transmits the combined signal back to the central station via an antenna. In this manner, the central station knows the identity of the patient because of the RF frequency or by use of another code and also knows the location of the patient because the patient received the transmitted beacon signal and interleaved that signal with the EKG data. In the system of this application, the same antenna distribution is utilized, but each antenna has a separate signature.

In FIG. 1, there are antennas 10, 11 and N shown. These antennas are distributed throughout the hospital at various locations in the hospital and for example, the antennas may be on different floors and in different rooms. Each antenna as for example antenna 10 maybe associated with an amplifying or preprocessing stage 30. Module 30 may just be a coupling network as an impedance matching device or an amplifier. The output of module 30 or the antenna output 10 is coupled to an antenna signature module 31. As seen in FIG. 1, the antenna signature (ANT SIGN) module 31 functions as follows. Each antenna as antenna 10, 11 and N is associated with a separate antenna signature module as modules 31, 33 and 35. The antenna signature module as will be explained adds a unique signature to all signals received by the associated antenna. In the preferred embodiment, each antenna signature module, as 31, 33 and 35, may include an AM or FM modulator which operates at a particular designated frequency as will be explained. In this manner, each received signal from an antenna is modulated with a discrete frequency only assigned to that antenna. Thus, the output from antenna 11, is modulated by a first frequency via the modulator 33. The output of antenna N is modulated by still another frequency via antenna signature module 35. The outputs of the antenna signature modules are directed to a processor 36 which is a power combiner. The power combiner is the minimum circuit requirement for an economical system configuration. These signals may be processed or further amplified or modified in module 36 and are then directed via a transmission line 37 to a central processing station 38. The central processing station may be the central nurse's location and can include a radio receiver, and central processor 38 which can further process the received signals. Thus, the processor will separate the signals and to provide a display 40 of each patient's EKG together with the indication of the location of the patient. The display can be implemented as indicated by means of a typical CRT, as a graphic display or can be a hard copy display provided by a printer display 41.

The invention operates as follows. Each of the antenna modules as 10, 11 and N are positioned in the ceilings, on the walls, in the corridors or at any desired location within the hospital. Each of the antennas can receive the signals transmitted or radiated by patient transmitters 21. When a patient is close to an antenna the signal received by the antenna will be stronger than the signal received by antennas which are not as close to the patient. In this manner, the central processor 38 when detecting a strong signal provides an indication that that patient is very close to an antenna. The processor can analyze the signature contained in the strong signal to determine from which antenna the signal originated. This is because of the fact that each antenna is associated with antenna signature module such as module 31 for antenna 10, module 33 for antenna 11 and module 35 for antenna N. Thus, each signal is provided with a antenna signature frequency for each individual antenna. This signal is detected and the system immediately knows at which antenna the patient is located.

Furthermore, since the patient has a unique RF frequency, the system immediately knows the identity of the patient. The system conventionally decodes the digital data transmitted to provide the patient's EKG data and the signature information is also decoded to indicate the location of the patient. As one can see, the system therefore requires no additional receiver for the patient transmitter, which simplifies the transmitter worn by the patient and increases its portable operating life. The existing antennas as 10, 11 and N are modified by including an antenna signature module for each of the antennas.

Referring to FIG. 2 there is shown a more detailed diagram of an antenna configuration with an antenna signature module operative to place a small amount of amplitude modulation at a different frequency for each antenna. The signature module modulates the RF signal received by the antenna with a different frequency for each antenna. Referring to FIG. 2 there is shown a plurality of antennas as 60, 61 and 62. While only three antennas are shown it is of course understood that many more antennas can be implemented and are in fact utilized. The antennas 60, 61 and 62 are distributed throughout a hospital or other location and may be mounted on the ceiling or on the walls and so on. The antennas are conveniently spaced so that a patient can always be in contact with one or more antennas. Each antenna 60, 61 and 62 are associated with a modulator 63, 64 and 65. The modulators are conventional designs and in this example are amplitude modulators. Thus, the signal received by each antenna is modulated by means of a local oscillator frequency 66, 67 and 68 for modulators 63, 64 and 65. The local oscillator signal from oscillator 66, 67 and 68 is a relatively low frequency signal which operates to amplitude modulate the received RF signal. Thus, the RF signal which is received by antenna 60 is modulated with a small amount of amplitude modulation at a relatively low frequency. As a typical example local oscillator 66 may operate at a frequency of 100 Hz. Local oscillator 67 operates at a frequency of 101 Hz, local oscillator 68 operates at a frequency of 102 Hz . . . etc. Thus, each of the RF signals received by each of the antennas 60, 61 and 62 is modulated by a low frequency signal which differs from the adjacent antenna frequency signal by one or more cycles. While the examples of 100, 101 and 102 Hz have been given it is of course understood that these frequencies can vary. It is indicated that a low frequency be utilized but such frequencies can for example be 200 Hz from oscillator 66, 202 Hz from oscillator 67, 204 Hz from oscillator 68 and so on. It is, of course, understood that other frequencies can be employed including adequate spacing between the frequencies to enable easy detection. Utilizing modern filtering techniques, as digital filters or employing FFT spectrum analysis one can discriminate between such low frequencies with one cycle differences. Such techniques for analyzing frequency transmissions and for determining small frequency differences are well known. The objective of a patient monitoring system is to distribute the antennas in such a manner that the patient is always within the range of at least one antenna. Thus, a patient such as patient 30 of FIG. 1 may be transmitting signals which are picked up by more than one antenna. As shown in FIG. 1, the patient 30 is transmitting signals to antennas 10, 11 and N. As one can ascertain, the patient transmits at a predetermined RF frequency which is designated strictly for that patient. This signal for example may be in the range of 200 MHz. Each patient has his own RF frequency assigned. For example, patient #1 may be assigned a frequency of 200 MHz, patient #2, 201 MHz, patient #3, 203 MHz and so on.

Assume the patient 30 of FIG. 1 is closest to antenna 10. Thus, the signal from the RF transmitter 21 is received at the greatest amplitude at antenna 10. The antennas are positioned within the area so that a patient is always close enough to at least one antenna to enable the system to provide an accurate location. As one can ascertain, the first thing the system has to determine is the detection of a strong carrier or RF frequency received from the antenna system. Thus, as seen in FIG. 2 and 1 each of the antenna outputs which emanate from the respective modulators 63, 64 and 65 are directed to the input of a power combiner module 69 which can also be a processor or multiplexer. In this manner, the signals from the various antennas are combined in the combiner 69 and transmitted via a transmission link 73, which may be a wire, infrared, microwave or other link to a central station processor 70. The central station processor 70 measures each of the received signals from antennas 60, 61 and 62. The processor 70 includes a plurality of narrow band radio receivers, one for each patient RF signal. In this manner, the central station processor operates to selectively filter the signal from combiner 69 to provide selected RF signals indicative of patient signals.

The RF data is demodulated in a conventional manner and the digital data is converted to an analog signal. Furthermore, the amplitude modulation associated with the RF signal is demodulated and detected. In this manner, it is now known that the patient with the particular RF carrier is near antenna 10. Thus, this information is developed by the central station where the patient identification is indicated in module 71 with the patient location indicated in module 72. As seen, the patient identification (ID) and the patient location are known. The EKG or other vital sign data is converted to analog form and is displayed on a suitable monitor or display. The patient location and identity can also be displayed.

It is understood that while amplitude modulators (AM) 63, 64 and 65 are shown in FIG. 2 other types of modulators can be employed as well. For example, one can use frequency modulation (FM) for each of the modulators to provide the antenna signature. One can also employ a pulse code modulation scheme or other schemes whereby a particular signal or a unique antenna code is added to the RF signal via the antenna signature modules as 31, 33 and 35. In this manner, each antenna when receiving an RF signal will interleave a signature signal indicative of the antenna location.

Referring to FIG. 3, modulator 82 which is associated with antenna 80 includes an oscillator which operates at 100.5 Hz. Modulator 83 associated with antenna 81 has a modulator which operates to amplitude modulate the RF signal at 101.5 Hz. The signals received by antennas 80 and 81 are shown as sinusoidal RF signals. Both output signals are combined in a power combiner module 84. The output of module 84 is directed to the input of amplifier 85. Amplifier 85 is connected to a transmission line or other line 86 to a power divider 87. The output of module 87 provides the composite RF signals each of which is associated with the amplitude modulation of 100.5 Hz and 101.5 Hz. As one can readily ascertain, each of the antenna modulators 82 and 83 provides an AM modulation on the received RF carrier which modulation component can be detected. In this manner the exact location of the patient in regard to a fixed or predetermined antenna position is known.

Thus, as explained, each antenna has a unique signature which may be in the form of an amplitude modulation or frequency modulation which is impressed on a received RF carrier. The system after detecting a strong carrier at the frequency of a particular patient's transmitter can now detect the modulation on the carrier to determine which antenna the patient is near. The monitored data on the RF carrier provides the information to produce an EKG or other vital sign signal as well.

Figure 4:
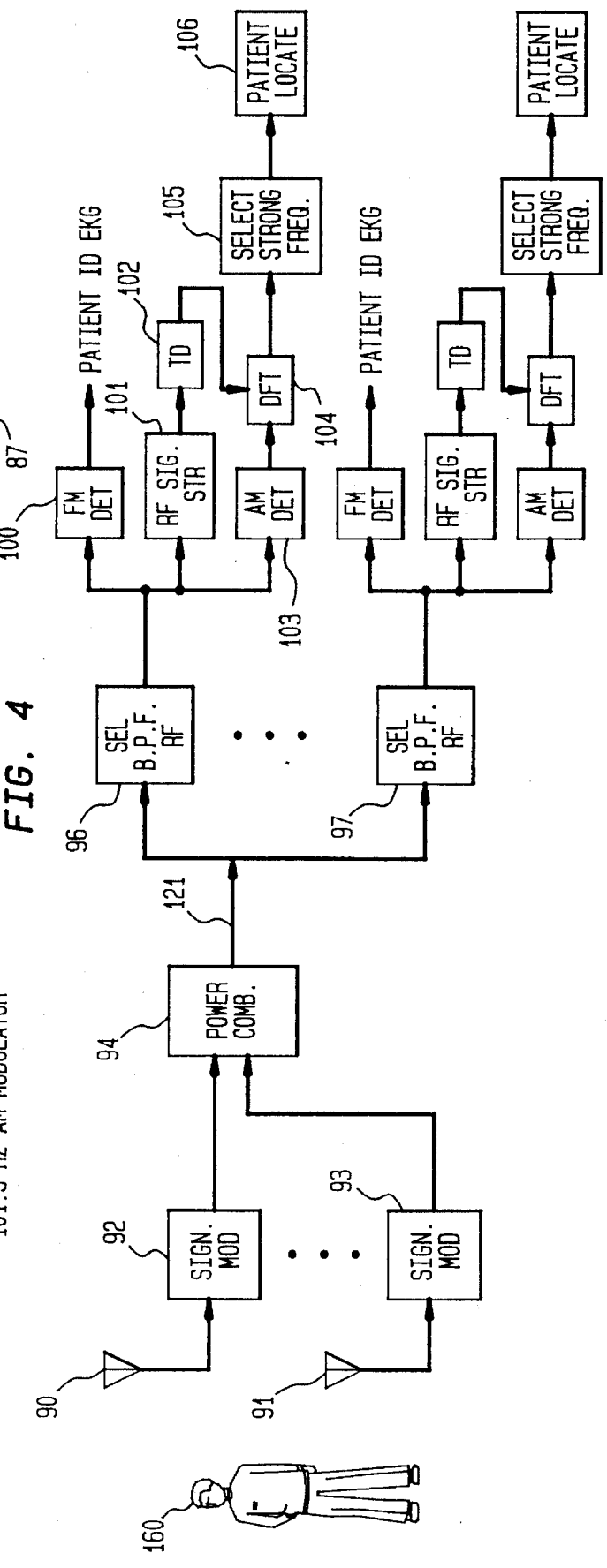
FIG. 4 is a block diagram showing a system for monitoring patient location by selective frequency allocation.

Referring to FIG. 4 there is shown antennas 90 and 91. These antennas are employed to represent the distribution of a plurality of antennas throughout an institution. Essentially as explained, such antennas are conventionally installed so that a patient 160 is always near a given antenna. The given antenna, of course, is the antenna which is receiving the strongest signal. Each antenna is associated with a signature module such as module 92 for antenna 90 and module 93 for antenna 91. The patient 160, as indicated, has a transmitter. The patient's transmitter transmits a typical RF signal which may be in the 200 MHz range. In any event, RF signals can be selected in the 400 MHz telemetry range or at lower frequencies as between 70 and 100 MHz. Reference is made to the above-noted patents as 4,958,645 and for 4,981,141 which describe typical RF frequencies which can be employed.

In particular, U.S. Pat. No. 4,958,645 describes typical telemetry transmitter and receiving characteristics which are employed in typical systems. Thus, the patient 160 transmits a modulated RF signal which is received by antenna 90. This signal is applied to the input of the signature module 92 where a suitable modulation is impressed upon the signal indicative of antenna 90. All antenna signals are modulated by the respective signature modulator and the outputs of the signature modulators as modulators 92 and 93 are directed to the inputs of a power combiner 94. The output of the power combiner 94 is coupled to a transmission link 121 which as indicated above may be of many sorts such as a cable link, an infrared link or various other transmission means. The output of the power combiner 94 via the transmission link 121 is directed to a plurality or bank of selected narrow bend RF filters such as 96 or 97. There is a separate bandpass filter as 96 and 97 for each of the assigned or allocated RF signals. Since each patient is assigned a different RF frequency, then each patient is associated with a separate filter. Thus, the output from a bandpass filter, as 96 and 97, immediately identifies the patient. Assume that patient 160 is associated with RF frequency indicative of bandpass filter 96 and is close to antenna 90. Thus, antenna receives the signal which is sent by combiner 94 to the filter bank. The bandpass filter 96 passes the RF signal. Note, the bandpass filters 96 and 97 may in fact comprise circuits for hetrodyning the RF signal to a lower frequency, thereby allowing a simpler bandpass filter design. The RF signal is directed to an FM detector 100. The FM detector responds to the modulation on the RF signal as is conventional, to produce at the output a patient ID EKG. The modulation on the RF carrier represents the vital sign information of the patient such as the EKG and may also contain other information. The output from the selective bandpass filter 96 is also coupled to the input of an RF signal strength circuit 101. The circuit 101 may include amplifier circuit which has an output coupled to a threshold detector 102. The function of circuits 101 and 102 is to determine whether the RF signal is above an acceptable limit. As one will ascertain, the patient's transmitter transmits signals at given power level. Thus, certain signals above a given power level are true patient signals while other signals below the threshold may be due to noise or spurious signals and so on. If the detector 102 receives such a signal of a given level then the detector operates to bias a Discrete Fourier Transform (DFT) module 104.

The output of selective bandpass filter 96 is also directed to the input of an AM detector 103. The AM detector operates to demodulate the received RF carrier signal to detect the low frequency signal indicative of the antenna signature. The output of the AM detector 103 is applied to the input of the DFT module 104 which is activated or operated when the strength of the incoming RF signal exceeds a predetermined level. The operation of a Discrete Fourier Transform or DFT is well understood in the state of the art. Essentially, the module 104 operates to scan the output from the AM detector 103 to determine the exact frequency of the signal emanating from the amplitude modulation detector 103. The module 105 selects the strongest output signal based on the DFT analysis. As it is understood, the DFT analysis can be implemented by conventional techniques which are well known in the art and essentially involve spectrum analysis. This may be accomplished by a DFT or a Fast Fourier Transform (FFT) which is processed by a microprocessor or signal processor. The DFT operates to analyze the signal from the amplitude detector to provide an accurate indication of the frequency of that signal, as indicated by module 105.

The amplitude modulation on the RF carrier is indicative of the antenna that the patient is nearest and hence defines the patient location, as is indicated by module 106. It is, of course, seen that the bandpass filter 97 passes a completely different RF frequency and is associated with the same components as described above. It is also understood that one can utilize other techniques which operate to analyze the RF signals to determine each separate RF component to determine the amplitude modulation on each component. Such techniques which relate to spectrum analyzers and associated modules are well known in the state of the art.

As described above, the present system is especially useful in regard to hospital operations since the location of the patient is known while the patient's vital signs are being monitored. The system can monitor the patient's vital signs continuously by displaying them and can track the patient's location due to the fact that each antenna the patient transmits to has a separate signature associated with it. The system can operate to monitor the EKG of a patient and determine when the patient is experiencing difficulty. Since the location of the patient is also known, then the appropriate hospital staff can be directed to administer to the patient. This system can also be utilized to locate persons in shopping malls and so on. In this manner, antennas would be placed throughout the structuring as in the ceilings or roofs or otherwise in regard to large shopping complexes or other areas where the location of persons is desired to be monitored.

Thus, it is understood, that while particular examples have been described it should be apparent to those skilled in the art that many modifications can be made without departing from the scope and intent of the invention.

What is claimed is:

1. A telemetry system for monitoring at least one vital sign of each one of a plurality of patients, as well as a physical location within an operating area for each patient being so monitored, comprising:

a plurality of patient monitoring transmitters, each transmitter adapted for being worn by a different one of said plurality of patients and for transmitting as a patient signal an RF signal which has a different RF carrier frequency allocated to each of said plurality of patients, each patient signal containing data indicative of at least one monitored vital sign of the patient wearing the transmitter, a plurality of antennas located in fixed positions throughout the operating area, each of the antennas having an input operative for receiving the patient signal transmitted by each transmitter and an output for directing the patient signal so received to a central location, which central location analyzes the patient signal for providing data indicative of the at least one monitored vital sign of the patient wearing the transmitter; and a plurality of antenna signature means, a different one of each of said antenna signature means being coupled to a respective different one of each of said plurality of antennas for generating a unique antenna identification signal for each antenna it is coupled to, which unique antenna identification signal is combined by said antenna signature means with each patient signal received by said antenna for forming a combined patient signal which is sent to said central location, said central location analyzing the combined patient signal so as to determine which unique antenna identification signal was combined with the patient signal, said determination indicating which antenna of said plurality of antennas located in fixed positions throughout the operating area transmitted the combined patient signal, thereby indicating the location within said operating area of the patient transmitter which transmitted the patient signal.

2. The system according to claim 1, wherein:

each one of said plurality of antenna signature means includes a modulator means having an input coupled to a respective one of each antenna output for applying a modulation to any patient signal received thereby, and a separate local oscillator coupled to a respective one of each modulator means and operative for causing each modulator means to apply a separate modulation frequency to any patient signal received thereby, which modulation frequency is indicative of a unique signature for each antenna; and each said modulator means having an output for providing as the combined patient signal any received patient signal modulated by said modulation frequency.

3. The system according to claim 2, wherein said modulation frequencies are in a range between 100 and 300 Hz.

4. The system according to claim 2, wherein said modulator means includes an amplitude modulator.

5. The system according to claim 2, wherein said modulator means includes a frequency modulator.

6. The system according to claim 1 further including:

receiving means for receiving said combined signal, said receiving means including means for bandpass filtering said combined signal to determine an RF carrier frequency of the patient signal and therefore a patient allocated to said RF carrier frequency, and means for detecting the unique antenna identification signal of said combined signal to determine a given one antenna of said plurality of antennas and therefore an indication of a patient location.

7. The system according to claim 6, wherein said means for bandpass filtering said signal includes a hetrodyning means for translating the RF carrier frequency to a lower frequency.

8. The system according to claim 1, wherein:

said antenna signature means includes a location code generator means coupled to each antenna, for combining a given location code with signals received by said antenna, where said location code provides an indication of location for each antenna.

9. In a patient monitoring telemetry system employing a plurality of antennas located in fixed positions throughout an operating area and where a mobile patient wears a transmitter capable of transmitting a patient signal containing data indicative of at least one monitored vital sign of said patient being monitored, said antennas adapted to receive said transmitted patient signal for directing the transmitted patient signal to a central location to provide data indicative of the at least one monitored vital sign of said patient, the improvement in combination therewith of apparatus for providing said central location with information indicative of a location of said patient within said operating area as determined by said patient being located near a given one antenna in said plurality, said apparatus comprising:

antenna signature means coupled to each antenna and operative for providing a unique signal for each antenna coupled thereto, which unique signal is combined with a received patient signal by said antenna for forming a combined signal, whereby each antenna of said plurality has a unique signal which is impressed upon any received patient signal to enable said central location to determine which antenna in said plurality transmitted the combined signal and therefore indicative of a location for said patient within said operating area; and threshold detection means coupled to said antenna signature means for detecting an amplitude of said combined signal so as to only direct combined signals exceeding a predetermined amplitude threshold to said central location.

10. A patient monitoring telemetry system for remotely and continuously monitoring patients within a given area, said system comprising:

a plurality of patient transmitters, each transmitter adapted to be mounted on a patient and including means for collecting patient data and each transmitter having an antenna for continuously radiating a patient signal indicative of said patient data, a plurality of antennas each positioned apart from one another and located at predetermined positions throughout said given area, a plurality of antenna signature meant, each one associated with one of said antennas and operative for combining an antenna signature signal with any patient signal received by said associated antenna for generating a combined signal, said signature signal being different for each antenna and thereby each being indicative of a specific one of said antennas which is located at a predetermined position in said given area, and receiving means coupled to said antennas for continuously receiving the combined signal from said antennas, and including means for detecting said antenna signature signal and said patient signal to simultaneously and continuously provide an output indicative of a location of said patient with regard to any one of said antennas and patient data of said patient.

11. The system according to claim 10, wherein said antenna signature means includes modulator means for applying a modulation to any patient signal received thereby, one modulator means for each antenna, and a separate local oscillator associated with each modulator means and operative to provide a separate modulation frequency for each modulator means and therefore for each antenna, said modulator means having one input for receiving said associated antenna signal and for providing at an output the combined signal which is said received patient signal modulated by said separate modulation frequency for said antenna.

12. The system according to claim 11, where said modulator means includes an amplitude modulator.

13. The system according to claim 11, wherein said modulator means includes a frequency modulator.

14. The system according to claim 11, wherein said modulation frequency is between 100 and 300 Hz.

15. The system according to claim 10, wherein each patient transmitter is allocated a unique frequency different from another patient transmitter frequency whereby said allocated frequency is definitive of a given patient.

16. The system according to claim 15, wherein said unique frequencies are RF frequencies selected in a range between 70 and 500 MHz.

17. The system according to claim 10 including:

threshold detecting means responsive to the combined signals from said antennas for selecting only those combined signals which have a magnitude which exceeds a predetermined threshold, whereby a greatest magnitude combined signal for a given patient will be selected from only one antenna of a plurality of antennas receiving said patient signal.

* * * * *